United States Patent

Guérémy et al.

[11] 3,984,431
[45] Oct. 5, 1976

[54] DERIVATIVES OF PYRAZOLE-5-ACETIC ACID

[76] Inventors: Claude Guérémy, 3, rue Daumesnil, Houilles 78; Christian Renault, 3, rue de la Justice, Epinay 73, both of France

[22] Filed: June 23, 1975

[21] Appl. No.: 589,513

Related U.S. Application Data

[63] Continuation of Ser. No. 340,964, March 14, 1973, abandoned.

[30] Foreign Application Priority Data

Mar. 15, 1972 United Kingdom............... 12182/72

[52] U.S. Cl.............................. 260/310 R; 424/273; 260/247.5 E
[51] Int. Cl.².................................... C07D 231/14
[58] Field of Search ............................... 260/310 R

[56] References Cited
UNITED STATES PATENTS
3,704,241  11/1972  Noguchi et al.................. 260/310 R FOREIGN PATENTS OR APPLICATIONS
1,946,370  4/1971  Germany....................... 260/310 R

*Primary Examiner*—Natalie Trousof
*Attorney, Agent, or Firm*—Haseltine, Lake & Waters

[57] ABSTRACT

Compounds having anti-inflammatory and antipyretic action have the general formula

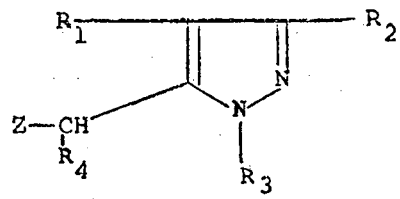

in which each of $R_1$ and $R_2$ is a phenyl group which may be substituted by a halogen atom, an alkyl or alkoxy group having 1 to 4 carbon atoms or a trifluoromethyl group, $R_3$ is a straight or branched chain saturated or unsaturated aliphatic hydrocarbon group or a cycloaliphatic hydrocarbon group having 3 to 7 carbon atoms, or a benzyl or phenyl group which benzyl or phenyl groups may be substituted in the benzene ring by a halogen atom, an alkyl or alkoxy group having 1 to 4 carbon atoms or a trifluoromethyl group or by any two of these substituents, $R_4$ is a hydrogen atom or an alkyl group having 1 to 4 carbon atoms and A is a group having one of the formulae —COOH, —COOR$_5$ and —CONR$_6$R$_7$ in which $R_5$ is an alkyl group having 1 to 4 carbon atoms or a benzyl group and each of $R_6$ and $R_7$ is a hydrogen atom or an alkyl group having 1 to 4 carbon atoms or $R_6$ and $R_7$ taken together with the nitrogen atom to which they are attached represents a pyrrolidino, a piperidino or a morpholino group.

2 Claims, No Drawings

DERIVATIVES OF PYRAZOLE-5-ACETIC ACID

This application is a continuation of application Ser. No. 340,964 filed Mar. 14, 1973, now abandoned, and claims the priority of the application filed in Great Britain on Mar. 15, 1972.

This invention relates to a group of chemical compounds which are derivatives of pyrazole-5-acetic acid which are useful in human medicine in particular on account of their anti-inflammatory and antipyretic action. The invention also relates to methods of preparing these compounds.

The compounds correspond to the general formula (I):

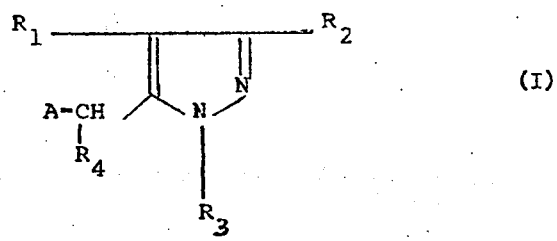

in which $R_1$ and $R_2$, which may be the same or different, each represent a phenyl group, which may be substituted by a halogen atom, an alkyl or alkoxy group having from 1 to 4 carbon atoms, or a trifluoromethyl group, $R_3$ is a saturated or unsaturated straight or branched chain aliphatic or cycloaliphatic hydrocarbon grouping having from 3 to 7 carbon atoms, a benzyl or phenyl grouping which may be substituted in the benzene ring by a halogen atom, an alkyl or alkoxy group having from 1 to 4 carbon atoms or a trifluoromethyl group, or by any two of said substituents, $R_4$ is a hydrogen atom or an alkyl group having from 1 to 4 carbon atoms and A represents a group having one of the formulae:

—COOH

—COOR$_5$

—CONR$_6$R$_7$ in which $R_5$ is an alkyl group having from 1 to 4 carbon atoms or a benzyl group, and each of $R_6$ and $R_7$ is a hydrogen atom or an alkyl group having 1 to 4 carbon atom or $R_6$ and $R_7$ taken together with the nitrogen atom to which they are attached represent a pyrrolidino, piperidino or morpholino group.

There are described below several methods for preparing the compounds having the general formula (I) in which the symbol A represents the carboxyl group. The preparation of the corresponding esters or amides may be performed by methods which are known per se and which enable the carboxylic group to be converted into a —COOR$_5$ or —CONR$_6$R$_7$ group. (See R. B. WAGNER et al., 1965 "Synthetic Organic Chemistry", John Wiley & Sons, Pp. 479 and 565). Esters and amides having the general formula (I) also form intermediate products in certain of the methods for preparing the carboxylic acids described below.

METHOD 1

Preparation of carboxylic acids having the general formula (I) by hydrolysis of a functional derivative of an appropriately substituted acid having the general formula (II):

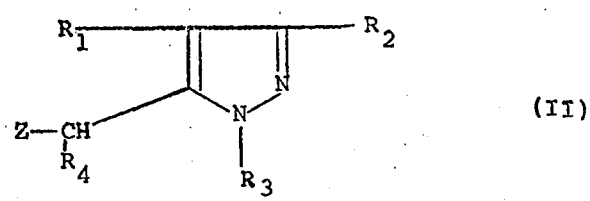

in which Z is a functional grouping which can be hydrolyzed to a carboxylic acid group: esters, nitriles, amides and thioamides are especially useful in this method.

The hydrolysis of such derivatives is performed under the usual conditions; the process takes place, for example, in an aqueous alkaline medium, conveniently in the presence of a water-miscible organic solvent such as ethanol or ethylene glycol, and generally under reflux. The process may also take place in a strongly acid aqueous medium, conveniently in the presence of a water-miscible organic solvent such as acetic acid or dioxan. In this case the concentration of the acid used and the reaction temperature vary according to the starting materials used and more especially according to the nature of the functional group Z; the esters are generally hydrolysed in a concentrated acid medium at moderate temperature, frequently at ambient temperature. The nitriles amides and thioamides are generally hydrolysed in a more or less concentrated acid medium, for example at a concentration of from 5N to 15N, and generally under reflux.

METHOD 2

Preparation of carboxylic acids having the general formula (I) by decarboxylation of malonic acid derivatives having the general formula (III).

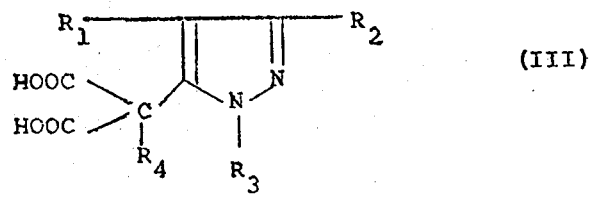

The decarboxylation of such derivatives is performed under the usual conditions. The product is, for example, heated approximately to or above its melting point, or alternatively refluxed in an inert organic solvent which has a high boiling point.

The process also takes place in an alkaline medium or an acid medium, usually under the conditions described for the hydrolysis of the nitriles and amides.

Amongst the functional derivatives having the general formula (II) those derivatives in which Z represents:

—COOR₅

—C—N

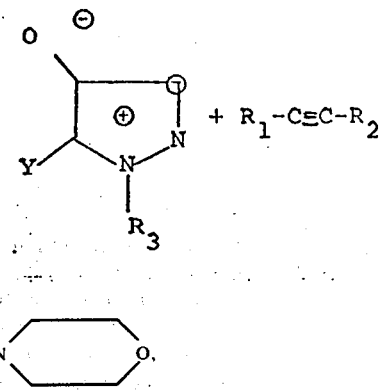

and R₄ represents a hydrogen atom, may be used as starting materials in method 1.

The thioamide derivatives of morpholine are prepared by the Willgerodt reaction from ketones having the general formula (IV)

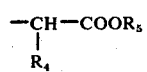

(IV)

The procedure involves heating the ketone (IV) under reflux in morpholine in the presence of an excess of powdered sulphur in accordance with the standard method.

The synthesis of the starting products for the preparation of carboxylic acids (I) by method 1 or 2 utilises various known processes, for example those described by L. C. BEHR et al. in "Pyrazoles, pyrazolines, pyrazolidines, indazoles and condensed rings" published by Interscience, 1967.

The following three processes may conveniently be employed:

PROCESS A

1–3 Dipolar addition of acetylene derivatives to sydnones having the general formula (V), in accordance with the following scheme:

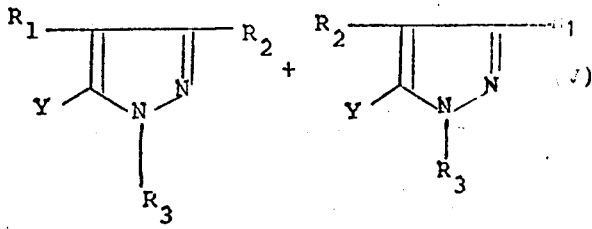

In general formula (V), Y represents one of the following groupings:

—CH—COR₅
  |
  R₄

—CO—CH₃

The reaction is carried out by heating the sydnone in the disubstituted acetylene derivative, or in the presence of the disubstituted acetylene derivative dissolved in an inert solvent such as xylene, tetrahydronaphthalene, para-cymene, chlorobenzene, mesitylene or decahydronaphthalene. The preferred temperatures lie between 100° and 250° C. The reactants may be used in equimolar properties but it is preferred to use an excess of the acetylene derivative. In this way two isomers are usually obtained, one of which usually preponderates. The products may be separated by known methods such as fractional crystallisation, distillation or chromotography.

PROCESS B

Conversion of carboxylic acid estes having the general formula (VI) into homologous nitriles having the general formula (VII) in accordance with the following scheme:

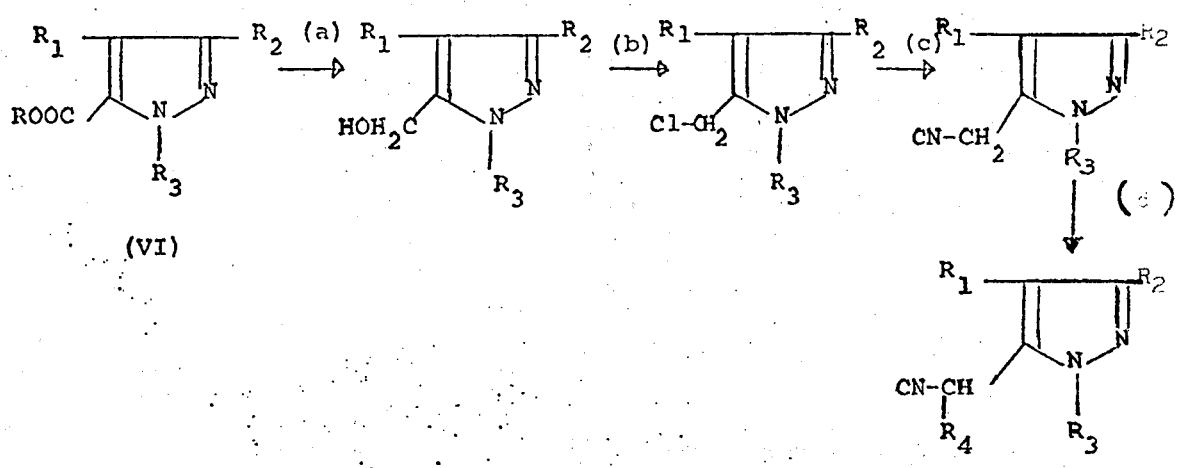

The first step (a) consists in reducing the ester (VI) with an appropriate metal hydride such as aluminum hydride and lithium hydride dissolved in diethyl ether or tetrahydrofuran. A modication consists in reducing the corresponding carboxylic acid under the same conditions. The product is the corresponding alcohol. The second step (b) consists in converting the alcohol obtained in the first step into the corresponding halide preferably a chloro derivative, by the action of a chlorinating agent such as thionyl chloride in the presence or absence of an inert solvent, such as chloroform, generally under reflux. The third step (c) consists in converting the chloride obtained in the second step into a nitrile by reaction with a metal cyanide, preferably an alkali metal cyanide, in the presence of an inert solvent such as acetone, dimethylformamide, aqueous ethanol or dimethylsulfoxide, at a temperature between 50° and 160° C. (d) If $R_4$ is other than a hydrogen atom, the next step consists in alkylating with an alkylating reagent $R_4X$ (in which X represents an esterifying group for example, a halogen atom) in the presence of an alkaline reacting agent. The procedure is advantageously to make the sodium derivative of the nitrile prepared in the third step using sodium amide in liquid ammonia or a hydrocarbon such as benzene, toluene or xylene, the alkylating reagent being introduced either before or after the sodium amide.

PROCESS C

Preparation of malonic derivatives having the general formula (III) from the corresponding nitriles or esters, in accordance with the reactions:

in which R and $R^1$ represent like or unlike alkyl groups, usually methyl or ethyl groups. This hydrolysis may be carried out by methods known per se, i.e. in alkaline or acid medium.

Depending upon the reaction conditions, the malonic derivative (III) may be isolated before decarboxylation or may be decarboxylated directly under the conditions of hydrolysis, thus leading directly to the acid (I). In an alkaline medium at moderately raised temperatures for example under reflux in aqueous ethanol in the presence of potash, the potassium salt of the malonic derivative is obtained and the acid having the general formula (III) may be isolated by acidification. On the other hand, in an acid medium, for example under reflux in aqueous sulphuric acid, or at high temperature, the acid (I) is generally obtained directly by decarboxylation of the malonic derivative (III) in situ.

The intermediates required for carrying out processes A, B and C may themselves be prepared by known processes, by analogy with the preparaton of known products described in the literature; more especially the processes indicated below may be used:

a. Preparation of the sydnones having the general formula (V), in accordance with the methods described in, for example: F. H. C. Stewart, Chemical Reviews, volume 64, page 129 (1964) and the literature referred to therein.

b. Preparation of the esters of pyrazole-carboxylic acids having the general formula (VI), in accordance with the methods described by L. C. Behr et al loc cit.

Two reactions in particular may advantageously be used:

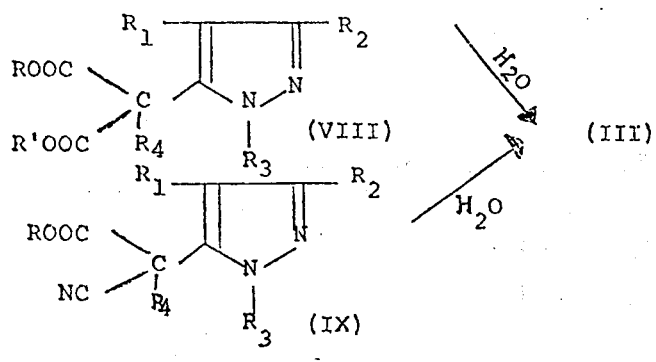

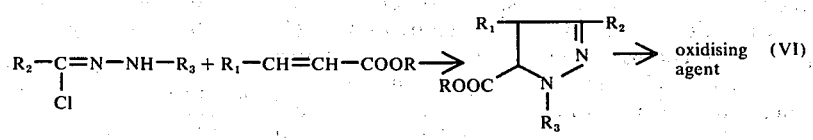

this method may conveniently be employed when $R_1$ and $R_2$ are different.

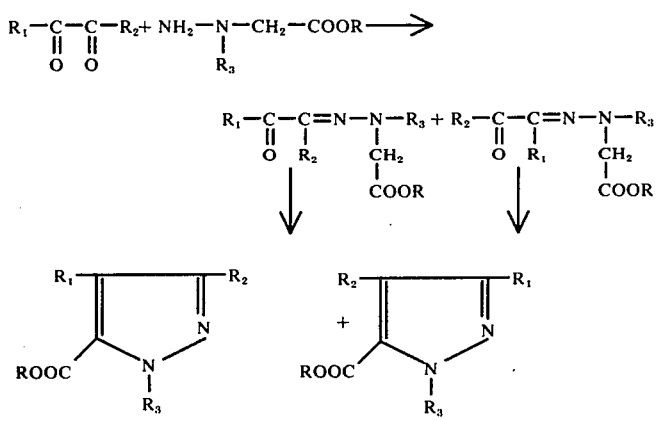

This method may conveniently be employed when $R_1$ and $R_2$ are the same; a single product is then obtained.

c. Preparation of malonic esters (VIII) and malonic nitriles (IX) in accordance with the standard methods the principle of which is shown diagrammatically below:

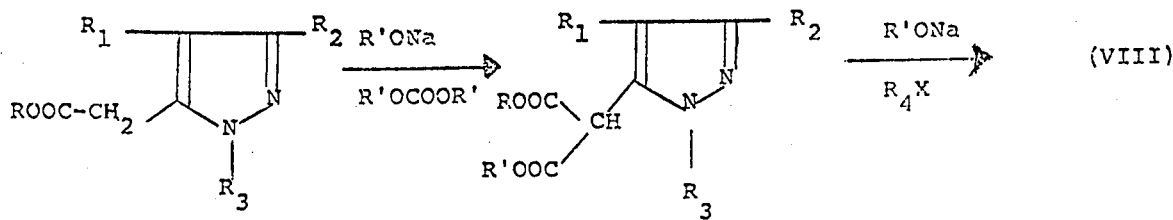

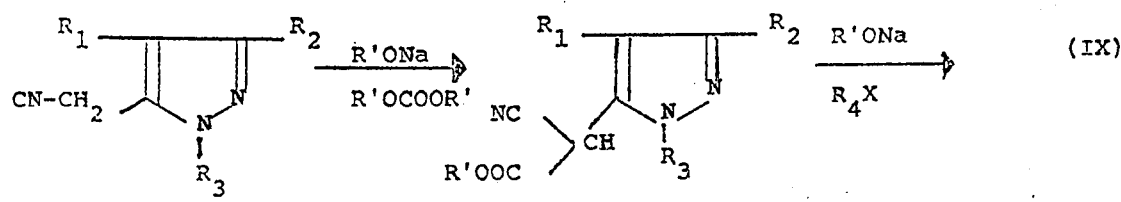

When $R_4$ is other than a hydrogen atom the products having the general formula (I) are obtained in the form of racemic mixtures. Optically active isomers are obtained by resolving the racemic mixtures by standard procedures. In particular, fractional distillation of the carboxylic acid salts having the general formula (I) may be performed using the salts with optically active amines such as alkaloids (strychnine, cinchonidine, quinine, and so on), or optically resolved amines and amino-alcohols conventionally used for carrying out such separations.

Broadly speaking, the compounds of the invention may be purified by conventional methods such as distillation, crystallisation or chromatography.

These compounds are useful in humal therapeutics, particularly as anti-inflammatory and antipyretic agents.

The doses will naturally depend upon the treatment and the method and the duration of administration, but the total daily oral or rectal dose will generally be 100 to 800 mg of active compound in the case of an adult. The compounds may be used as they are or in the form of pharmaceutical compositions containing standard media and diluents, as well as with customary pharmaceutical adjuvants such as suitable coating preserving, moisturising, dissolving, lubricating, colouring, and flavouring agents.

A typical example is given below of a composition for a tablet having a total weight of 500 mg:

| | |
|---|---|
| 1-benzyl-3,4-diphenylpyrazolyl-5-acetic acid | 250 mg |
| starch | 190 mg |
| colloidal silica | 50 mg |
| magnesium stearate | 10 mg |

The following examples illustrate the nature of the invention

EXAMPLE 1

1-benzyl-3,4-diphenylpyrazolyl-5-acetic acid

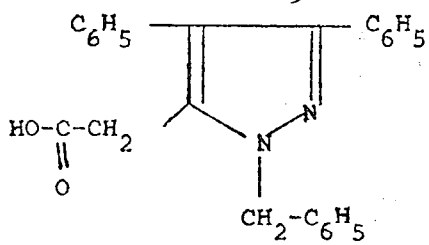 (Method 1-A)

A mixture of 24.8 grams of methyl 3-benzyl-sydnone-4-acetic acid and 35.6 grams of diphenylacetylene dissolved in 50 ml of xylene is heated at 140° C for 65 hours. The solvent is removed at 60° C under reduced pressure and the residue is dissolved in 200 ml of N soda and 200 ml of acetone. This mixture is heated at 60° C for seven hours and the acetone is then removed under reduced pressure. After the addition of 300 ml of water the aqueous phase is extracted with 300 ml of benzene. The benzene solution is first washed with 250 ml of water and then with 100 ml of water. The aqueous extracts are combined and washed three times with 150 ml of benzene. The aqueous solution is then acidified with 35 ml of 6N hydrochloric acid and the resulting precipitate is extracted first with 350 ml of benzene and then twice with 250 ml thereof. The benzene solution is washed four times with 100 ml of water, dried over anhydrous magnesium sulphate and then evaporated to dryness under reduced pressure. 12.5 grams of crude product are obtained, which is recrystallised from 60 ml of boiling acetonitrile. There are thus obtained 5.8 grams of 1-benzyl-3,4-diphenyl-pyrazolyl-5-acetic acid melting at 182° C.

The methyl 3-benzyl-4-sydnoneacetate may be prepared as described in Japanese Patent. No. 70/21509 dated 21st July 1970.

EXAMPLE 2

1-benzyl-3,4-diphenylpyrazolyl-5-acetic acid (Method 1-3)

2 grams of 1-benzyl-3,4-diphenylpyrazolyl-5-acetonitrile are dissolved in 4 ml of concentrated sulphuric acid and 4 ml of water. The resulting solution is heated for 30 minutes under reflux and is then cooled to ambient temperature and 8.7 ml of water added thereto. The gum which precipitates is extracted with 50 ml of hot chloroform. The organic phase is twice washed with a total of 60 ml. of water. The organic phase is dried over magnesium sulphate and the chloroform removed under reduced pressure. The residue is dissolved in 15 ml of N caustic soda solution and the aqueous phase is acidified with 2 ml of concentrated hydrochloric acid and the precipitate obtained is filtered, twice washed with a total of 20 ml of water, and then twice washed with a total of 40 ml of diisopropyl ether. 1.9 grams of a product are obtained which, when recrystallised from 13 volumes of acetonitrile, give 1.5 grams of 1-benzyl-3,4-diphenylpyrazolyl-5-acetic acid melting at 181°–182° C.

The 1-benzyl-3,4-diphenylpyrazolyl-5-acetonitrile used was prepared in the following manner:

10 grams of 1-benzyl-3,4-diphenyl-5-chloromethyl-pyrazole dissolved in 80 ml of dimethylsulfoxide are heated with 1.72 grams of sodium cyanide for 5 hours at 70°C while being stirred. The solution obtained is cooled to ambient temperature and poured into 800 ml of water. The oil which separates out is thrice extracted with a total of 300 ml of chloroform. The combined organic extracts are dried over magnesium sulphate and evaporated under reduced pressure. The gum obtained as residue is dissolved in 100 ml of diisopropyl ether. 8 grams of 1-benzyl-3,4-diphenylpyrazolyl-5-acetonitrile melting at 181° C are thus obtained.

The 1-benzyl-3,4-diphenyl-5-chloromethylpyrazole used is prepared in the following manner:

60 grams of 1-benzyl-3,4-diphenyl-5-hydroxymethyl-pyrazole dissolved in 150 ml of anhydrous chloroform are added to 51 ml of thionyl chloride dissolved in 450 ml of anhydrous chloroform, which has been cooled to −5° C. The solution is heated for 3 hours under reflux whilst being stirred. It is then cooled to ambient temperature and the chloroform is evapoated under reduced pressure. The residue is dissolved in 200 ml of petroleum ether and then suspended in 100 ml of diisopropyl ether. 53.4 grams of 1-benzyl-3,4-diphenyl-5-chloromethylpyrazole melting at 99° C are thus obtained.

The 1-benzyl-3,4-diphenyl-5-hydroxymethyl pyrazole used as starting material is prepared in the following manner:

228 Grams of crude ethyl 1-benzyl-3,4-diphenyl-pyrazole-5-carboxylate (prepared as described below) dissolved in 3200 ml of anhydrous diethyl ether are added, at 0°C and under a nitrogen atmosphere, to 47 grams of lithium aluminium hydride suspended in 1600 ml of anhydrous diethyl ether. The solution is stirred overnight at ambient temperature and then cooled to 0° C, whereupon 55 ml of water, 20.2 ml of 10N soda and 83 ml of water are slowly and successively added under a nitrogen atmosphere, and the resulting precipitate is filtered. The filtrate is evaporated under reduced pressure and the residue is dissolved in 360 ml of di-isopropyl ether. 1 -Benzyl-3,4-diphenyl-5-hydroxymethyl-pyrazole melting at 138° C is thus obtained.

The ethyl 1-benzyl-3,4-diphenyl pyrazole-5-carboxylate used is prepared in the following manner:

407 grams of crude ethyl alpha-benzoylbenzylidene-N-benzylhydrazinyl acetate (see the preparation below) dissolved in 1500 ml of ethanol are added to a solution of sodium ethylate in ethanol prepared by adding 47 grams of sodium to 1500 ml of ethanol. The solution is heated for 1.5 hours under reflux, then cooled to ambient temperature and the ethanol is evaporated under reduced pressure. The residue is dissolved in a mixture of 2500 ml of water and 2000 ml of chloroform. The organic phase is separated and dried over magnesium sulphate and the chloroform is evaporated under reduced pressure. 238 grams of crude ethyl 1-benzyl-3,4-diphenylpyrazole-5-carboxylate in the form of a yellow oil are thus obtained.

The ethyl alpha-benzylbenzylidene-N-benzoylhydrazinylacetate is prepared in the following manner:

135 ml of concentrated hydrochloric acid are added drop by drop to 310 grams of crude ethyl 1-benzylhydrazinylacetate (see the preparation below) suspended in 300 ml of water. 370 Grams of sodium acetate and 164 grams of benzyl dissolved in 1000 ml of ethanol are added to the limpid solution obtained. The resulting reaction mixture is heated for 4 hours under reflux and is then allowed to stand overnight at ambient temperature. It is then filtered and the filtrate evaporated under reduced pressure. The residue is dissolved in 1000 ml of water and the oil which separated out is thrice extracted with a total of 600 ml of diethyl ether. The combined ethereal extracts are dried over magnesium sulphate and the ether is evaporated under reduced pressure. 407 Grams of crude ethyl alpha-benzoyl-benzylidene-N-benzylhydrazinylacetate in the form of a yellow oil are thus obtained.

The ethyl benzyl hydrazinylacetate used in the above preparation is prepared in the following manner:

Over a period of 45 minutes, 222 grams of crude ethyl N-nitrosobenzylaminoacetate (see the preparation below) dissolved in a mixture of 385 ml of ethanol and 750 ml of 50% aqueous acetic acid are added to a suspension of 650 grams of zinc in a mixture of 375 ml of water and 415 ml of ethanol, which suspension has been cooled to 0° C. The solution is kept at 0° C for 30 minutes whilst being stirred and is then filtered. The precipitate is then washed with 1000 ml of iced water. The filtrate is made alkaline to pH 9 with a saturated solution of sodium carbonate. The resulting reaction mixture is filtered and the precipitate is washed first with 500 ml of water and then twice with a total of 1000 ml of chloroform. The filtrate is decanted and the aqueous phase is extracted four times with a total of 4000 ml of chloroform. The combined chloroform extracts are dried over magnesium sulphate and the chloroform is evaporated at ambient temperature under reduced pressure. 170 Grams of a yellow oil are thus obtained of which two-thirds is ethyl benzyl hydrazinylacetate and one-third is ethyl benzylaminoacetate.

The ethyl N-nitrosobenzylaminoacetate used in the above preparation is prepared in the following manner:

Over a period of 25 minutes 760 grams of ethyl benzylaminoacetate are added to a solution of 2000 ml of concentrated hydrochloric acid and 2000 ml of water while being stirred. The resulting solution is cooled to 0° C and 300 grams of sodium nitrite dissolved in 700 ml of water are introduced over a period of 30 minutes. After completion of this addition the reaction mixture is stirred at 0° C for 1.5 hours. The organic phase is separated and the aqueous phase is thrice extracted with a total of 3000 ml of diethyl ether. The combined organic phases are dried over magnesium sulphate and the ether is evaporated under reduced pressure. There are thus obtained 723 grams of crude ethyl N-nitrosobenzylaminoacetate in the form of an orange oil.

The ethyl N-benzylaminoacetate used is prepared in the following manner:

560 ml of ethyl bromoacetate are added whilst stirring at 0° C to 535 grams of benzylamine and 505 grams of triethylamine dissolved in 2500 ml of benzene over a period of 35 minutes. After 3 hours stirring at ambient temperature, the triethylamine hydrobromide which has formed is filtered. The filtrate is washed four times with a total of 4000 ml of water. The organic phase is dried over magnesium sulphate and the benzene is evaporated under reduced pressure. 900 grams of ethyl benzylaminoacetate in the form of a yellow oil are obtained.

EXAMPLE 3

1-isobutyl-3,4-diphenylpyrazolyl-5-acetic acid(Method 1-A)

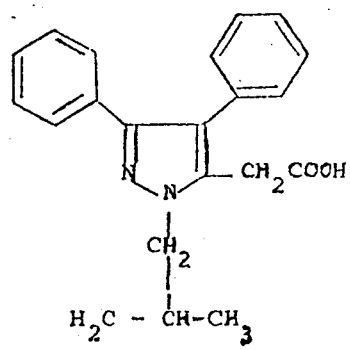

120 grams of methyl 3-isobutyl-4-sydnonylacetate and 110 grams of diphenylacetylene dissolved in 600 ml of xylene are heated under reflux whilst being stirred for 70 hours. The solution is cooled to ambient temperature and the xylene is evaporated under reduced pressure. The residue is dissolved in a mixture of 800 ml of N soda and 800 ml of acetone. The resulting solution is heated under reflux for 4 hours whilst stirring and is then cooled to ambient temperature and separated. The aqueous phase has 1000 ml of water added thereto and is then extracted thrice with a total of 900 ml of benzene. The aqueous phase is then made acid by the addition of 68 ml of concentrated hydrochloric acid. The oil which separates out is extracted five times with a total of 1000 ml of chloroform. The combined chloroform extracts are dried over magnesium sulphate and the chloroform is evaporated under reduced pressure. 78 grams of a brown oil are obtained which are submitted to chromatography upon silica gel using a mixture of 99 parts of chloroform to 1 part of methanol. After recrystallisation from acetonitrile, 1-isobutyl-3,4-diphenylpyrazolyl-5-acetic acid melting at 181° C is obtained.

The methyl 3-isobutyl-4-sydnonyl acetate used as starting material is prepared in the following manner:

Over a period of 15 minutes and whilst stirring 158 grams of methyl N-isobutyl-N-nitrosobeta-aspartate are added to 340 ml of acetic anhydride and then, drop by drop, 0.95 ml of 70% perchloric acid. The reaction mixture is then stirred for 2 hours at ambient temperature. The acetic anhydride is evaporated under reduced pressure, and the residue is then successively dissolved once in 100 ml of chloroform, thrice in 100 ml of benzene each time and twice in 100 ml of diethyl ether each time, the solvent being evaporated each time under reduced pressure. 155 Grams of red oil are obtained which are dissolved in 2 volumes of hot di-isopropyl ether and cooled. After 1 minute at 3°C the crystals which separate are filtered and there are thus obtained 78 grams of methyl 3-isobutyl-4-sydnonyl acetate melting at 39° C.

The methyl N-isobutyl-N-nitroso-beta-aspartate used is prepared in the following manner:

Over a period of 10 minutes 860 ml of concentrated hydrochloric acid are added to a suspension of 340 grams of methyl N-isobutyl-beta-aspartate in 860 ml of water whilst stirring. The solution is cooled to 0° C and 128 grams of sodium nitrite dissolved in 280 ml of water are introduced over a period of 1 hour 20 minutes. The reaction mixture is stirred for 2 hours at 0° C and extraction is then carried out thrice with a total of 3000 ml of diethyl ether. The organic phase is thrice washed with a total of 1500 ml of water, dried over magnesium sulphate and the ether evaporated under reduced pressure. The residue, when dissolved in a mixture of 1400 ml of petroleum ether and 230 ml of ether, gives, after cooling to 3° C, 325 grams of methyl N-isobutyl-N-nitroso-beta-aspartate melting at 95° C. The methyl N-isobutyl-beta-aspartate used is prepared in the following manner:

50 grams of maleic anhydride and 180 ml of methanol are heated for 1 hour under reflux while stirring. The reaction mixture is cooled to ambient temperature and the excess methanol is evaporated under reduced pressure. 67 grams of monomethyl maleate are obtained. The maleic ester is then cooled to 0° C after which 90 ml of triethylamine and then 34 grams of isobutylamine are introduced over a period of 1 hour. The reaction mixture is heated under reflux for 1 hour, then cooled to 50°C and 200 ml of acetone added; as a result of filtering off the crystals which separate there are obtained 73.7 grams of methyl N-isobutyl-beta-aspartate melting at 250°C.

EXAMPLE 4

1-isobutyl-3,4-diphenylpyrazolyl-5-acetic acid
(Method 1-B)

28.5 grams of soda dissolved in 100 ml of water are added to 102.5 grams of 1-isobutyl-3,4-diphenyl-5-pyrazolyl-acetonitrile dissolved in 1000 ml of water. The resulting reaction mixture is heated for 20 hours under reflux whilst being stirred. It is then cooled to ambient temperature and the methanol is evaporated under reduced pressure. The crystalline product obtained is dissolved in 1000 ml of water and the aqueous phase is thrice washed with a total of 600 ml of diethyl ether. The aqueous phase is acidified with 50 ml of concentrated hydrochloric acid and the precipitate which is obtained is filtered on a glass frit and washed thrice with a total of 1500 ml of water. After recrystallisation from 7 volumes of acetonitrile, 87 grams of 1-isobutyl-3,4-diphenylpyrazolyl-5-acetic acid melting at 181°C are obtained.

The 1-isobutyl-3,4-diphenyl-5-pyrazolyl-acetonitrile used is prepared in the following manner:

72.4 grams of 1-isobutyl-3,4-diphenyl-5-pyrazole and 13.7 grams of sodium cyanide are heated for 4 hours at 70°C in 450 ml of dimethylsulfoxide. The reaction product is cooled to ambient temperature and poured into 4500 ml of water. The oil which separates out is extracted thrice with a total of 1500 ml of diethyl ether. The combined ethereal extracts are dried over magnesium sulphate and then evaporated under reduced pressure. The gum obtained is triturated with a mixture of 300 ml of petroleum ether and 100 ml of di-isopropyl ether. The crystalline product obtained is filtered and 63.1 grams of 1-isobutyl-3,4-diphenylpyrazolyl-5-acetonitrile are thus obtained, melting at 100°C.

The 1-isobutyl-3,4-diphenyl-5-chloromethylpyrazole is prepared in the following manner:

Over a period of 15 minutes, 74.8 grams of 1-isobutyl-3,4-diphenyl-5-hydroxymethylpyrazole dissolved in 400 ml of chloroform are added to a solution of 71 ml of thionyl chloride in 300 ml of chloroform which solution has previously been cooled to 0°C. The reaction mixture is heated under reflux for 4 hours whilst being stirred and is then cooled to ambient temperature and the chloroform is then evaporated under reduced pressure. The red oil obtained is treated with 200 ml of 30-50 petroleum ether and there are thus obtained 72.4 grams of 1-isobutyl-3,4-diphenyl-5-chloromethylpyrazole melting at 92°C.

The 1-isobutyl-3,4-diphenyl-5-hydroxymethylpyrazole used is prepared in the following manner:

74 grams of crude 1-isobutyl-3,4-diphenylpyrazolyl-5-carboxylate are added to a stirred suspension of 16.5 grams of lithium aluminium hydride in 500 ml of diethyl ether which has previously been cooled to 0°C and over which an atmosphere of nitrogen is maintained. The reaction mixture is stirred overnight at ambient temperature, then 19.3 ml of water, 7.1 ml of 10N soda and 64 ml of water are successively introduced, at 0°C and whilst maintaining a nitrogen atmosphere. The resulting precipitate is filtered, the filtrate evaporated under reduced pressure and a crystalline product is obtained which, after washing with 2 volumes of petroleum ether, gives 28 grams of 1-isobutyl-3,4-diphenyl-5-hydroxymethylpyrazole melting at 154°C.

The ethyl 1-isobutyl-3,4-diphenylpyrazolyl-5-carboxylate is prepared in the following manner:

117 grams of ethyl alpha-benzoyl-benzylidene-N-isobutylhydrazinylacetate dissolved in 500 ml of ethanol are added to a solution of sodium ethylate in ethanol prepared by adding 14.7 grams of sodium to 500 ml of absolute ethanol. The resulting solution is held under reflux for 2 hours whilst stirring. It is then cooled to ambient temperature and the ethanol evaporated under reduced pressure. The crystalline mass obtained is dispersed in 1000 ml of water and the oil which separates out is thrice extracted with a total of 600 ml of chloroform. The combined chloroform extracts are dried over magnesium sulphate and evaporated under reduced pressure to give 74 grams of crude ethyl 1-isobutyl-3,4-diphenylpyrazolyl-5-carboxylate in the form of a brown oil.

The ethyl alpha-benzoyl-benzylidene-N-isobutylhydrazinyl-acetate used is obtained in the following manner:

44 ml of concentrated hydrochloric acid are slowly added to 137.8 grams of crude ethyl 1-isobutylhydrazinylacetate (see the preparation below) in suspension in 110 ml of water. 119 grams of sodium acetate and 61 grams of benzil dissolved in 300 ml of ethanol are added to the clear solution obtained. The resulting solution is held under reflux for 3 hours whilst stirring and is then kept overnight at ambient temperature. It is then filtered and the filtrate evaporated under reduced pressure. The residue obtained is dissolved in 300 ml of water and the oil which separates out is twice extracted with a total of 400 ml of diethyl ether. The combined ethereal extracts are dried over magnesium sulphate and the ether evaporated under reduced pressure. There is thus obtained 117 grams of crude ethyl alpha-benzoyl-benzylidene N-isobutyl hydrazinylacetate in the form of a red oil.

The ethyl isobutyl hydrazinylacetate used is prepared in the following manner:

Over a period of 35 minutes, 300 grams of crude ethyl N-nitrosoisobutylamine acetate (see the preparation below) dissolved in a mixture of 320 ml of ethanol and 560 ml of 50% aqueous acetic acid are added to a suspension of 520 grams of zinc in 480 ml of ethanol precooled to 0°C. The reaction mixture is kept for 1.5 hours at 15°-20°C and then filtered. The precipitate collected is washed with 1000 ml of water. The filtrate is then made alkaline to pH 9 with 2000 ml of a saturated solution of sodium carbonate. The resulting mixture is filtered and the precipitate is washed with 1000 ml of chloroform. The filtrate is separated and the aqueous phase is extracted five times with a total of 5000 ml of chloroform. The chloroform extracts are combined, dried over magnesium sulphate and the chloroform is evaporated under reduced pressure. There is thus obtained 200 grams of a yellow oil of which two-thirds is ethyl isobutyl hydrazinylacetate and one-third is ethyl isobutylaminoacetate.

The ethyl N-nitrosoisobutylaminoacetate used is prepared in the following manner:

Over a period of 30 minutes 762 grams of ethyl isobutylaminoacetate are added to a solution of 2000 ml of concentrated hydrochloric acid and 2000 ml of water. The resulting solution is cooled to 0°C and 265 grams of sodium nitrite dissolved in 750 ml of water are added over a period of 30 minutes. The reaction mixture is stirred for 1.5 hours at 0°C and the oil which separates out is extracted four times with a total of 4000 ml of diethyl ether. The combined ethereal extracts are dried over magnesium sulphate and evaporated under reduced pressure. There is thus obtained 847 grams of crude ethyl N-nitrosoisobutylaminoacetate in the form of an orange oil.

The ethyl isobutylaminoacetate is prepared in the following manner:

During the course of 30 minutes 672 ml of ethyl bromoacetate are added to 600 ml of isobutylamine and 830 ml of triethylamine dissolved in 4000 ml of benzene kept at 0°C. After stirring for three hours at ambient temperature, the triethylamine hydrobromide formed is filtered. The filtrate is thrice washed with a total of 3000 ml of water, dried over magnesium sulphate and evaporated under reduced pressure. There is thus obtained 762 grams of ethyl isobutylaminoacetate in the form of a yellow oil.

EXAMPLE 5

1,3,4-triphenylpyrazolyl-5-acetic acid (Method 1-B)

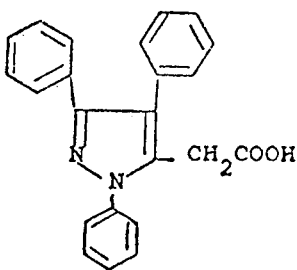

4.6 grams of soda dissolved in 19 ml of water are added to 19 grams of 1,3,4-triphenylpyrazolyl-5-acetonitrile dissolved in 200 ml of ethanol. The reaction mixture is heated for 20 hours under reflux whilst stirring and is then cooled to ambient temperature and the ethanol evaporated under reduced pressure. The crystalline product obtained is dissolved in 1000 ml of water and the oil which separates out is extracted with 200 ml of diethyl ether. The aqueous phase is made acid with 8 ml of concentrated hydrochloric acid, the precipitate which forms is collected and dissolved in 300 ml of chloroform, the chloroform solution is dried over magnesium sulphate and then evaporated under reduced pressure. A crystalline product is obtained which, after recrystallisation from 6 volumes of acetonitrile, gives 7 grams of 1,3,4-triphenylpyrasolyl-5-acetic acid melting at 200°C.

The 1,3,4-triphenylpyrazolyl-5-acetonitrile used is prepared in the following manner:

24.2 grams of 1,3,4-triphenyl-5-chloromethylpyrazole and 4.3 grams of sodium cyanide are heated for 4 hours at 70°C in 250 ml of dimethyl sulfoxide. The reaction mixture is cooled to ambient temperature and poured into 2500 ml of water. The oil which separates out is extracted four times with a total of 500 ml of diethyl ether. The combined ethereal extracts are dried over magnesium sulphate and evaporated under reduced pressure. The crystalline mass obtained is suspended in 80 ml of di-isopropyl ether and there is thus obtained 20 grams of 1,3,4-triphenylpyrazolyl-5-acetonitrile melting at 144°C.

The 1,3,4-triphenyl-5-chloromethylpyrazole is prepared in the following manner:

Over a period of 10 minutes, 27.5 grams of 1,3,4triphenyl-5-hydroxymethylpyrazole dissolved in 275 ml of chloroform are added to a solution of 24.4 ml of thionyl chloride in 100 ml of chloroform previously cooled to 0°C. The reaction mixture is heated for 1.5 hours under reflux whilst stirring, it is then cooled to ambient temperature and the chloroform evaporated under reduced pressure. The oil obtained is crystallised from 80 ml of benzene. There is thus obtained 24.4 grams of 1,3,4-triphenyl-5-chloromethyl-pyrazole melting at 122°C.

The 1,3,4-triphenyl-5-hydroxymethyl-pyrazole used is prepared in the following manner:

43 grams of 1,3,4-triphenylpyrazole-5-carboxylic acid dissolved in 400 ml of tetrahydrofuran are added, whilst stirring, to a suspension of 9.6 grams of lithium aluminium hydride in 1000 ml of diethyl ether cooled to 0°C and under a nitrogen atmosphere. The reaction mixture is stirred overnight at ambient temperature, and then 11.3 ml of water, 4.2 ml of 10N soda and 38 ml of water are slowly and successively added at 0°C under a nitrogen atmosphere. The reaction mixture is filtered and the filtrate is evaporated under reduced pressure. There is thus obtained 27.9 grams of 1,3,4-triphenyl-5-hydroxy-methylpyrazole in the form of a thick oil.

The 1,3,4-triphenyl-5-pyrazole carboxylic acid used is prepared in the following manner:

151.6 grams of crude ethyl alpha-benzoyl-benzylidene-N-phenyl hydrazinylacetate (see the preparation below) dissolved in 700 ml of ethanol are added to a solution of sodium ethylate in ethanol prepared by adding 18 grams of sodium to 700 ml of ethanol. The reaction mixture is held under reflux for 2.5 hours and is then cooled to ambient temperature and the ethanol evaporated under reduced pressure. The crystalline mass obtained is dissolved in 1000 ml of water and the oil which separates out is extracted twice with a total of 1000 ml of chloroform. The aqueous phase is made acid with 30 ml of concentrated hydrochloric acid and the precipitate formed is filtered. There is thus obtained 43.6 grams of 1,3,4-triphenylpyrazole-5-carboxylic acid melting at 190°C.

17

The ethyl benzoyl-benzylidene-N-phenyl hydrazinylacetate used is prepared in the following manner:

44 ml of concentrated hydrochloric acid are slowly added to 19 grams of crude ethyl 1-phenylhydrazinylacetate (see the preparation below) suspended in 90 ml of water. 116 grams of sodium acetate and 48 grams of benzyl dissolved in 200 ml of ethanol are added to the clear solution obtained. The reaction mixture is heated under reflux for 3 hours whilst stirring and is then kept overnight at ambient temperature. It is then filtered and the filtrate is evaporated under reduced pressure. The residue is dissolved in 300 ml of water and the oil which separates out is thrice extracted with a total of 900 ml of diethyl ether. The combined ethereal extracts are dried over magnesium sulphate and evaporated under reduced pressure. There is thus obtained 151.6 grams of crude ethyl alpha-benzoyl-benzylidene-N-phenylhydrazinylacetate in the form of an orange coloured oil.

The ethyl 1-phenylhydrazinylacetate used is prepared in the following manner:

Over a period of 1 hour, 12 grams of ethyl N-nitrosophenylaminoacetate dissolved in 45 ml of ethanol and 80 ml of acetic acid are added to a suspension of 75 grams of zinc in 115 ml of ethanol and 40 ml of water cooled to 0°C. The reaction mixture is stirred for 1 hour at 0°C and is then filtered. The precipitate which collects is washed with 200 ml of water. The filtrate is made alkaline with 600 ml of a saturated solution of sodium carbonate. The precipitate which separates is filtered and washed with 200 ml of chloroform. The aqueous phase is separated and extracted four times with a total of 200 ml of chloroform. The combined chloroform extracts are dried over magnesium sulphate and evaporated under reduced pressure. 8 grams of oil are thus obtained of which two-thirds is ethyl 1-phenylhydrazinylacetate and one-third is ethyl phenylaminoacetate.

The ethyl N-nitrosophenyl aminoacetate used is prepared in the following manner:

Over a period of 30 minutes 14.5 grams of ethyl phenylaminoacetate are added to a solution of 50 ml of concentrated hydrochloric acid and 50 ml of water cooled to 0°C. The reaction mixture is cooled to 0°C and 6.15 grams of sodium nitrite dissolved in 20 ml of water are added whilst stirring. The reaction mixture is stirred for 1 hour and the oil which separates out is extracted five times with a total of 250 ml of diethyl ether. The combined ethereal extracts are dried over magnesium sulphate and evaporated under reduced pressure. There is thus obtained 13.5 grams of ethyl N-nitrosophenylaminoacetate in the form of an orange coloured oil.

The ethyl phenyl aminoacetate used is prepared in the following manner:

Over a period of 30 minutes and whilst stirring 11.2 ml of ethyl bromoacetate are added to 9.3 grams of aniline and 10.1 grams of triethylamine dissolved in 60 ml of benzene and cooled to 0°C. The reaction mixture is stirred for 3 hours at ambient temperature and the triethylamine hydrobromide formed is filtered off. The organic phase is washed with 100 ml of water and is then dried over magnesium sulphate. The benzene is evaporated under reduced pressure and there is thus obtained 15.5 grams of ethyl phenylaminoacetate in the form of a yellow oil.

18

EXAMPLE 6

Alpha [1-benzyl-3,4-diphenylpyrazolyl-5-]propionic acid (Method 1-B)

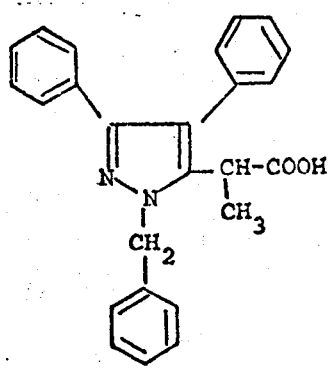

3.4 grams of alpha-[1-benzyl-3,4-diphenylpyrazolyl-5]propiononitrile are dissolved in 12 ml of concentrated acetic acid, 7 ml of concentrated sulphuric acid and 6 ml of water are added thereto and the reaction mixture is heated for 3 hours under reflux and then cooled to ambient temperature and 50 ml of water added. The gum which separates out is extracted thrice with a total of 60 ml of chloroform. The combined chloroform extracts are dried over magnesium sulphate and evaporated under reduced pressure. 3.6 Grams of a crystalline product are thus obtained which when recrystallized from 10 volumes of acetonitrile, gives 2.5 grams of alpha-[1-benzyl-3,4-diphenylpyrazolyl-5]propionic acid melting at 198°C.

The alpha-[1-benzyl-3,4-diphenylpyrazolyl-5-propiononitrile was prepared in the following manner:

1.25 ml of methyl iodide and 4.1 ml of a suspension of sodium amide in xylene (concentration — 17%) are added to 3.5 grams of 1-benzyl-3,4-diphenylpyrazolyl-5-acetonitrile dissolved in 50 ml of benzene. The reaction mixture is held under reflux for 48 hours whilst stirring and is then cooled to ambient temperature and the benzene distilled under reduced pressure. The residue obtained is then added to 50 ml of water. The oil which separates out is extracted thrice with 20 ml of chloroform each time. The combined chloroform extracts are dried over magnesium sulphate and then evaporated under reduced pressure. There is thus obtained 3.4 grams of alpha-[1-benzyl-3,4-diphenylpyrazolyl-5]propionitrile melting at 132°C.

The preparation of the 1-benzyl-3,4-diphenylpyrazolyl-5acetonitrile used is described in Example 2.

EXAMPLE 7

Alpha-[1-benzyl-3,4-diphenylpyrazolyl-5]propionic acid (Method 2-C)

A sodium ethylate solution obtained by dissolving 0.23 grams of sodium in 11 ml of ethanol is added to 3.5 grams of 1-benzyl-3,4-diphenylpyrazolyl-5-acetonitrile dissolved in 19 ml of ethyl carbonate while the temperature is maintained at 110°C. The ethanol is distilled during the addition. The reaction mixture is cooled to ambient temperature and the diethyl carbonate is distilled under reduced pressure. A gummy brown residue is obtained which is dissolved in 60 ml of ethanol and to which 2.4 ml of methyl iodide are then added. The resulting mixture is heated overnight under reflux in a nitrogen atmosphere, it is then cooled to ambient temperature and the ethanol is evaporated under reduced pressure. The doughy mass obtained is dissolved in 50 ml of water. The oil which separates out is then extracted thrice with a total of 60 ml of methylene chloride. The combined extracts are dried over magnesium sulphate and evaporated under reduced pressure to give 4.2 grams of a brown oil which is dissolved in a mixture of 11 ml of water and 11 ml of concentrated sulphuric acid. The reaction mixture is heated for 20 hours under reflux, it is then cooled to ambient temperature and the oil which separates out is extracted thrice with a total of 60 ml of methylene chloride. After the combined extracts have been dried over magnesium sulphate and evaporated under reduced pressure, 1 gram of alpha-[1-benzyl-3,4-diphenylpyrazolyl-5]propionic acid melting at 197°–198°C is obtained. The preparation of the 1-benzyl-3,4-diphenyl-5-pyrazole acetonitrile used is described in Example 2.

EXAMPLE 8

Alpha-[1-isobutyl-3,4-diphenylpyrazolyl-5]propionic acid (Method 2-C)

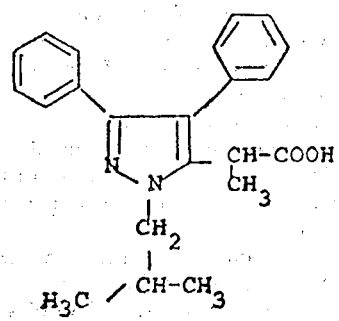

A sodium ethylate solution prepared from 0.41 grams of sodium and 10 ml of ethanol is slowly added to 4.75 grams of methyl 1-isobutyl-3,4-diphenylpyrazolyl-5-acetate dissolved in 15 ml of ethyl carbonate. The ethanol is distilled during the addition. The reaction mixture is cooled to ambient temperature and 30 ml of water and 2.5 ml of concentrated acetic acid are added thereto. The oil which separates out is extracted thrice with a total of 60 ml of diethyl ether. The combined ethereal extracts are twice washed with a total of 60 ml of water, dried over magnesium sulphate and the ether evaporated under reduced pressure to give 5 grams of red oil which are dissolved in 40 ml of ethanol. A sodium ethylate solution obtained by dissolving 0.294 grams of sodium in 10 ml of ethanol is added to this solution, and then 1.56 ml of methyl iodide. The reaction mixture is heated under reflux for 3 hours. It is then cooled to ambient temperature and the ethanol evaporated under reduced pressure. The doughy mass obtained is dissolved in 60 ml of water. The oil which separates out is extracted twice with a total of 60 ml of diethyl ether. The combined ethereal extracts are washed three times with a total of 60 ml of water, dried over magnesium sulphate and the ether is evaporated under reduced pressure to give 3 grams of red oil which are dissolved in 10 ml of ethanol after which 5 ml of 10N, washing soda and 10 ml of water are added to the solution. The reaction mixture is heated for 3 hours under reflux and is then cooled to ambient temperature and the ethanol evaporated under reduced pressure. The residue obtained is then dissolved in 20 ml of water and 20 ml of diethyl ether. The aqueous phase is separated and then made acid with 6 ml of concentrated hydrochloric acid. The oil which separates out is extracted twice with a total of 40 ml of chloroform. The combined chloroform extracts are dried over magnesium sulphate and the chloroform is evaporated under reduced pressure. The oil obtained is heated for 30 minutes at 230°C. There is thus obtained 1 gram of alpha- 1-isobutyl-3,4-diphenylpyrazolyl-5 propionic acid melting at 140°C.

The methyl 1-isobutyl-3,4-diphenylpyrazolyl-5-acetate used is prepared as described in example 4 by using methyl bromoacetate in place of ethyl bromoacetate. A product melting at 85°C is obtained. Below is given a brief summary of the pharmacological properties of the compounds of the present invention.

The anti-inflammatory action of the products was tested on the rat and the guinea-pig by oral administration and making use of three types of experimentally induced inflammation.

1. Carragheen induced odema; method of Winter Arch. intern. Pharmacod. volume 112, page 174 (1957)

2. Ultra-violet induced erythema; method of Winter Arch. intern. Pharmacod. volume 114, page 261 (1958)

3. The formation of granulomae caused by the subcutaneous implantation of pellets of cotton in the rat; method of Winter Journal of the American Pharmaceutical Association, Science Edition, Volume 46, page 515 (1957)

The analgesic action was tested in relation to the pain caused in the mouse by the subcutaneous injection of acetic acid. Method based upon that of Siegmund, Proceedings of the Society of Experimental Biology and Medicine, volume 75, page 729 (1957)

Antipyretic action was established on the pyretic rat by the Bianchi method. Arzneimittel Forschung, volume 17, page 246 (1967)

In all cases the products of the invention are compared to the following reference substances, aspirin, phenylbutazone, indomethacine. The results are given in the table which follows:

TABLE

| | 50% effective dose (mg/kg) | | | | | |
|---|---|---|---|---|---|---|
| METHOD | PRODUCT OF EXAMPLE 1 | PRODUCT OF EXAMPLE 3 | PRODUCT OF EXAMPLE 5 | PHENYLBUTAZONE | ASPIRIN | INDOMETHACINE |
| Pain (cramp) caused by acetic acid (mouse) | 150 | 180 | 90 | 110 | 130 | 5.5 |
| Carragheen induced oedema (rat) | 60 | 30 | 14 | 120 | 180 | 14 |
| Ultra-violet | | | | | | |

TABLE-continued

| METHOD | PRODUCT OF EXAMPLE 1 | PRODUCT OF EXAMPLE 3 | PRODUCT OF EXAMPLE 5 | PHENYLBUTAZONE | ASPIRIN | INDOMETHACINE |
|---|---|---|---|---|---|---|
| induced erythema (guinea-pig) | 1.6 | 1 | 3 | 8.5 | 50 | 1.5 |
| Cotton pellet granulema (rat) | 80 | 18 | 6 | 200 | — | 8 |
| Brewer's yeast induced pyrexia (rat) | 1 | 0.5 | 0.6 | 10 | 30 | 1.3 |

It is readily apparent from the above table that the product of example 5 is a powerful anti-inflammatory and anti-pyretic agent, and that it has a marked analgesic effect.

In this respect, the compound of example 5 may be considered at least equivalent to indomethacine, and much more powerful than phenylbutazone. The products of examples 1 and 3 are also active substances, although slightly less so than example 5, although the less active product, namely that of example 3, is still more powerful than phenylbutazone.

Broadly speaking, the compounds of the invention may be purified by conventional methods such as distillation, crystallisation or chromatography.

These compounds are useful in human therapeutics, particularly as antiinflammatory and antipyretic substances.

The doses will naturally depend upon the treatment, and the method and period of administration, but the total daily adult dose for oral or rectal administration will generally be from 100 to 800 mg. The compounds can be used as they are or in the form of pharmaceutical compositions which also contain standard media and diluents, as well as with normal pharmaceutical adjuvents such as suitable coating, preserving, moisturising, lubricating, solvating, colouring and flavouring agents.

Below is given an example of a composition which may be used for a tablet of 500 mg:

| | |
|---|---|
| [1-benzyl-3,4-diphenyl)pyrazolyl-5]acetic acid | 250 mg |
| starch | 190 mg |
| colloidal silica | 50 mg |
| magnesium stearate | 10 mg |

What is claimed is:
1. 1-Isobutyl-3,4-diphenypyrazolyl-5 acetic acid.
2. 1,3,4-triphenylpyrazolyl-5 acetic acid.

* * * * *